US009399107B2

(12) United States Patent
Ho et al.

(10) Patent No.: US 9,399,107 B2
(45) Date of Patent: *Jul. 26, 2016

(54) TEXTURED/POLISHED RESPIRATORY MASK SEAL AND MASK

(71) Applicant: KONINKLIJKE PHILIPS N.V., Eindhoven (NL)

(72) Inventors: Peter Chi Fai Ho, Pittsburgh, PA (US); Cornelis Petrus Hendriks, Eindhoven (NL); Rudolf Maria Jozef Voncken, Eindhoven (NL); Willem Potze, Geldrop (NL); Joyce Van Zanten, Waalre (NL); Nicolaas Petrus Willard, Valkenswaard (NL); Mareike Klee, Straelen (DE)

(73) Assignee: RIC INVESTMENTS, LLC, Wilmington, DE (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/156,759

(22) Filed: Jan. 16, 2014

(65) Prior Publication Data

US 2014/0130804 A1   May 15, 2014

Related U.S. Application Data

(63) Continuation of application No. 13/538,071, filed on Jun. 29, 2012, now Pat. No. 8,662,080, which is a continuation-in-part of application No. 12/623,460, filed on Nov. 23, 2009, now Pat. No. 8,230,861, which is a continuation of application No. 10/778,444, filed on Feb. 13, 2004, now Pat. No. 7,640,933.

(51) Int. Cl.
*A61M 16/06* (2006.01)
*A61M 16/08* (2006.01)
*A61M 16/00* (2006.01)

(52) U.S. Cl.
CPC ....... *A61M 16/0875* (2013.01); *A61M 16/0057* (2013.01); *A61M 16/06* (2013.01);
(Continued)

(58) Field of Classification Search
CPC ... A41D 13/05; A41D 13/11; A41D 13/1176; A61F 5/56; A61H 2205/082; A61H 9/00; A61H 9/005; A61M 16/0057; A61M 16/0488; A61M 16/049; A61M 16/0493; A61M 16/06; A61M 16/0605; A61M 16/0616; A61M 16/0622; A61M 16/0633; A61M 16/0666; A61M 16/0683; A61M 16/0688; A61M 16/0825; A61M 16/0875; A61M 2205/11; A61M 2210/0618; A61M 31/00; A61M 35/00; A62B 18/00; A62B 18/02; A62B 18/025; A62B 18/08; B23Q 3/00; B29C 43/02; B29C 43/021; B29L 2031/4835; B32B 27/00; B32B 7/06; B32B 7/12; B41M 3/14; B41M 5/506; B41M 5/508; B41M 5/5254; B44C 1/1712; B65C 5/04; C09J 7/02; C10L 1/328; D06H 1/02; D06P 1/004; D06P 5/003; D06P 5/007; D06Q 1/12; G06K 19/027; G09F 3/00; G09F 3/02; G09F 3/10; H01M 8/04164; H01M 8/0618; H01M 8/0625; Y10S 428/913; Y10S 428/914; Y10T 29/49895; Y10T 428/24802; Y10T 428/2813; Y10T 428/2817; Y10T 428/2822; Y10T 428/2826; Y10T 428/2839; Y10T 428/2848
USPC ............ 128/200.24, 202.17, 205.25, 206.12, 128/206.14, 206.18, 206.21, 206.23, 128/206.24, 206.25, 206.26, 206.27, 128/206.28, 207.13, 207.18, 857, 863
See application file for complete search history.

(56) References Cited

U.S. PATENT DOCUMENTS 3,330,273 A   7/1967   Bennett
3,827,433 A   8/1974   Shannon
(Continued)

FOREIGN PATENT DOCUMENTS

GB          2318500 A  *  4/1998  ............. A41D 20/00

OTHER PUBLICATIONS

"Rough" The American Heritage Dictionary of the English Language, 4th ed. 2000.

*Primary Examiner* — Annette Dixon
(74) *Attorney, Agent, or Firm* — Michael W. Haas

(57) ABSTRACT

A seal for a respiratory mask that includes a first end portion adapted to be coupled to a mask shell, a second end portion for sealing engagement with a face of a patient, and a sidewall extending between the first end portion and the second end portion. At least a portion of the second end portion includes a textured area having a predetermined pattern. The area of increased surface roughness provides the patient contacting portion of the seal with a silky feeling to maximize patient comfort and the effectiveness of the seal without impairing the sealing ability.

3 Claims, 7 Drawing Sheets

(52) U.S. Cl.
CPC ....... *A61M16/0616* (2014.02); *A61M 16/0622* (2014.02); *A61M 16/0633* (2014.02); *A61M 16/0666* (2013.01); *A61M 16/0683* (2013.01); *A61M 2210/0618* (2013.01)

(56) References Cited

U.S. PATENT DOCUMENTS

| | | | |
|---|---|---|---|
| 4,292,689 A * | 10/1981 | Townsend, Jr. | A61F 9/045 2/12 |
| 4,447,914 A | 5/1984 | Jannard | |
| 4,537,192 A | 8/1985 | Foster | |
| 4,698,852 A * | 10/1987 | Romero | A42B 3/00 2/171 |
| 4,730,915 A | 3/1988 | Jannard | |
| 4,945,575 A * | 8/1990 | Townsend | A61F 9/045 2/12 |
| 4,971,051 A | 11/1990 | Toffolon | |
| 5,243,971 A | 9/1993 | Sullivan | |
| 5,492,116 A | 2/1996 | Scarberry | |
| 5,520,613 A | 5/1996 | Copeland | |
| 5,540,223 A | 7/1996 | Starr | |
| 5,647,357 A | 7/1997 | Barnett | |
| 5,724,965 A | 3/1998 | Handke | |
| 5,884,624 A | 3/1999 | Barnett | |
| 6,397,847 B1 | 6/2002 | Scarberry | |
| 6,467,483 B1 | 10/2002 | Kopacko | |
| 6,851,425 B2 | 2/2005 | Paul et al. | |
| 7,066,179 B2 | 6/2006 | Eaton | |
| 7,069,932 B2 | 7/2006 | Eaton | |
| 7,640,933 B1 | 1/2010 | Ho | |
| 8,230,861 B2 | 7/2012 | Ho | |
| 2004/0244799 A1 | 12/2004 | Landis | |
| 2005/0076913 A1 | 4/2005 | Ho | |
| 2005/0126573 A1 | 6/2005 | Jaffre | |
| 2006/0225740 A1 | 10/2006 | Eaton | |
| 2006/0249157 A1 | 11/2006 | Eaton | |
| 2007/0009732 A1 | 1/2007 | Tsai | |
| 2007/0107733 A1 | 5/2007 | Ho | |
| 2011/0209701 A1 | 9/2011 | Derringer | |

* cited by examiner

TEXTURED/POLISHED RESPIRATORY MASK SEAL AND MASK

CROSS-REFERENCE TO RELATED APPLICATIONS

This application is a Continuation under 35 U.S.C. §120 of U.S. patent application Ser. No. 13/538,071, filed Jun. 29, 2012, which is a Continuation-in-Part under 35 U.S.C. §120 of U.S. patent application Ser. No. 12/623,460, filed Nov. 23, 2009, now U.S. Pat. No. 8,230,861, which is a Continuation of U.S. patent application Ser. No. 10/778,444, filed Feb. 13, 2004, now U.S. Pat. No. 7,640,933, the contents of each of which is incorporated herein by reference

BACKGROUND OF THE INVENTION

1. Field of the Invention

The present invention relates to a seal that has a textured patient-contacting surface to improve comfort during contact with the patient's face and a polished surface to maintain aesthetic appeal, and to a respiratory mask using such a seal.

2. Description of the Related Art

A variety of respiratory masks are known that have flexible seals and cover the nose, mouth, or both of a human patient. The seals, which are also commonly referred to as cushions, are intended to create a seal against the patient's face. Because of the sealing effect that is created, gases can be provided at a positive pressure within the mask for delivery to the airway of the patient.

The uses for such masks range from high altitude breathing, i.e., aviation applications, to mining and fire fighting applications, to various medical diagnostic and therapeutic applications. For example, such masks are used in the delivery of continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

A requisite of such respiratory masks is that they provide an effective seal against the patient's face to prevent leakage of the gas being supplied, while also providing a comfortable patient/seal interface. This problem is most crucial because such masks are typically worn for an extended period of time. One concern in such a situation is that a patient may avoid wearing an uncomfortable mask, defeating the purpose of the prescribed pressure support therapy.

Examples of conventional respiratory masks used in the medical field for providing a positive airway pressure to a patient include U.S. Pat. No. 5,243,971, which teaches a bubble-type of patient interface in which the seal is attached to a shell and extends from the shell in a concave fashion. Other conventional masks are disclosed, for example, in U.S. Pat. Nos. 5,540,223 and 6,467,483. A still further type of mask is described in U.S. Pat. No. 5,647,357, which uses a gel material as the seal or cushion to maximize patient comfort and sealing properties. U.S. Pat. No. 4,971,051 teaches a mask in which the seal includes multiple flaps, again to optimize patient comfort and the sealing property.

In each of these conventional seals and others, the patient-contacting surface of the seal or the flap is very smooth, which is also referred to as being highly polished. Polished surfaces can cause skin irritation in some patients. The present inventors opined that such irritation is the result of an inability of the skin underlying the polished to "breathe". That is moisture and/or heat may build up under the polished cushion. Polished surfaces also tend to feel sticky or tacky to the touch, causing the seal to stick to the patient's skin. This stickiness may cause the cushion to dislodge from the shell or faceplate to which the seal is mounted rather than shift on the patient if a torque or pulling force is applied on the mask

SUMMARY OF THE INVENTION

Accordingly, it is an object of the present invention to provide a seal for a respiratory mask that overcomes the shortcomings of conventional patient interface devices. This object is achieved according to one embodiment of the present invention by providing a seal for a respiratory mask that includes a first end portion adapted to be coupled to a mask shell, a second end portion for sealing engagement with a face of a patient, and a sidewall extending between the first end portion and the second end portion. At least a portion of the second end portion includes a textured area having a first rms surface roughness that is greater than a second rms surface roughness of a non-textured area of the seal. The first rms surface roughness being greater than the second rms surface roughness causes the patient contacting portion of the seal to have a silky feeling. This silkiness for the seal increases patient comfort and the effectiveness of the seal and is used by the patient without impairing the sealing ability of the cushion. Because the remaining portion of the seal has less surface roughness, it appears to be smooth and lightweight, enhancing the aesthetic appearance of the seal and, hence, user acceptance.

In another embodiment of the present invention, the seal includes a first end portion adapted to be coupled to a mask shell, a second end portion for sealing engagement with a face of a patient, and a sidewall extending between the first end portion and the second end portion. At least a first portion of the second end portion includes a first rms surface roughness that is greater than 700 microinches. In addition, at least a second portion of the second end portion of the seal or a first portion of the sidewall includes a second rms surface roughness that is less than 700 microinches. As noted above, this degree of surface roughness causes that portion of the seal to have a silky feel at the patient contacting surface of the seal, increasing patient comfort. It also prevents or reduces the sticky or tackiness associated with surfaces with less rms surface roughness.

It is yet another object of the present invention to provide a respiratory mask having a shell with a first opening adapted to be coupled to a patient circuit and a second opening, and a seal of either embodiment discussed above coupled to the shell generally at the second opening.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

DETAILED DESCRIPTION OF THE PRESENTLY PREFERRED EMBODIMENTS OF THE INVENTION

Figure 1:
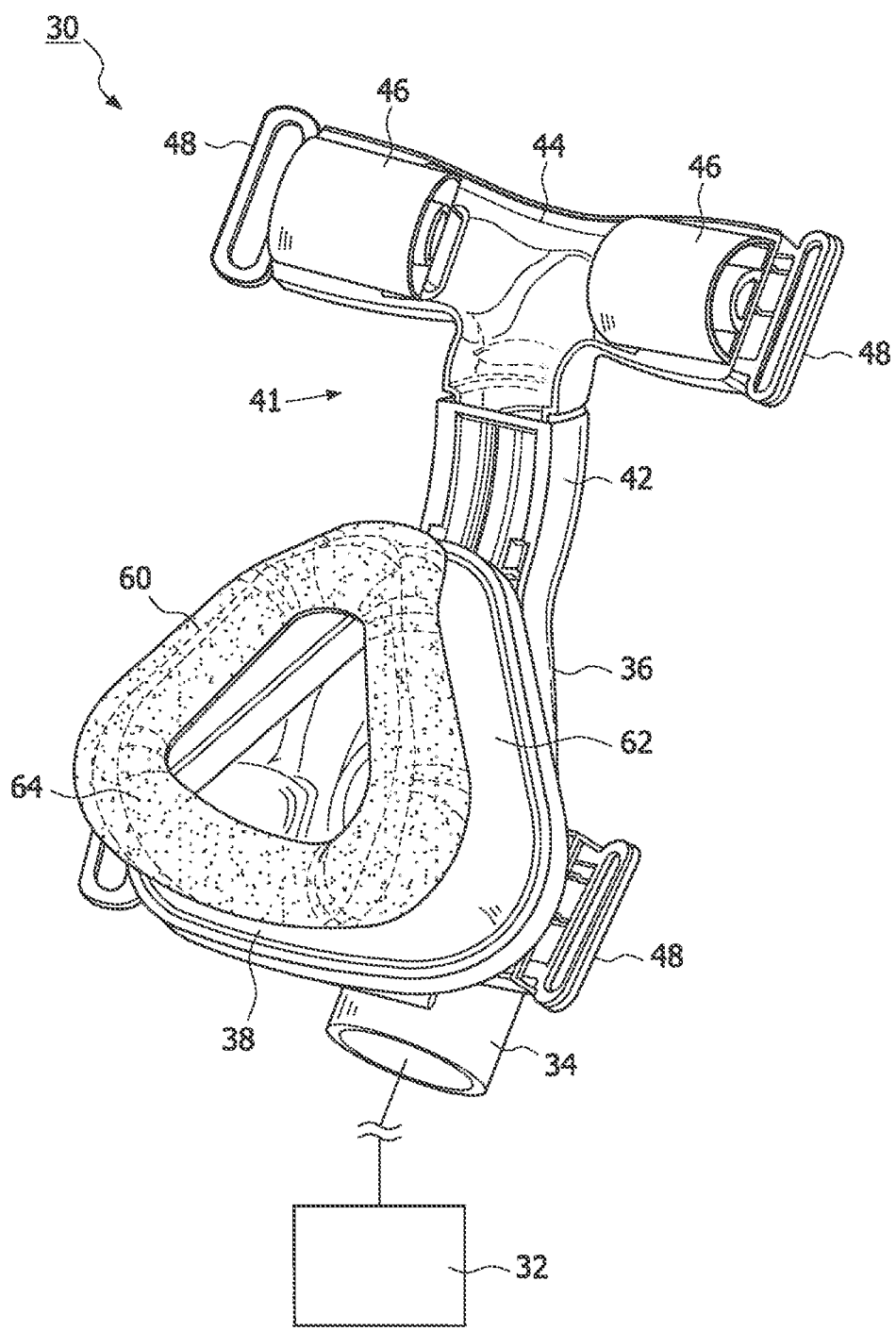
FIG. 1 is a perspective view of a respiratory mask according to the principles of the present invention shown schematically coupled to a pressure support system.
Figure 2:
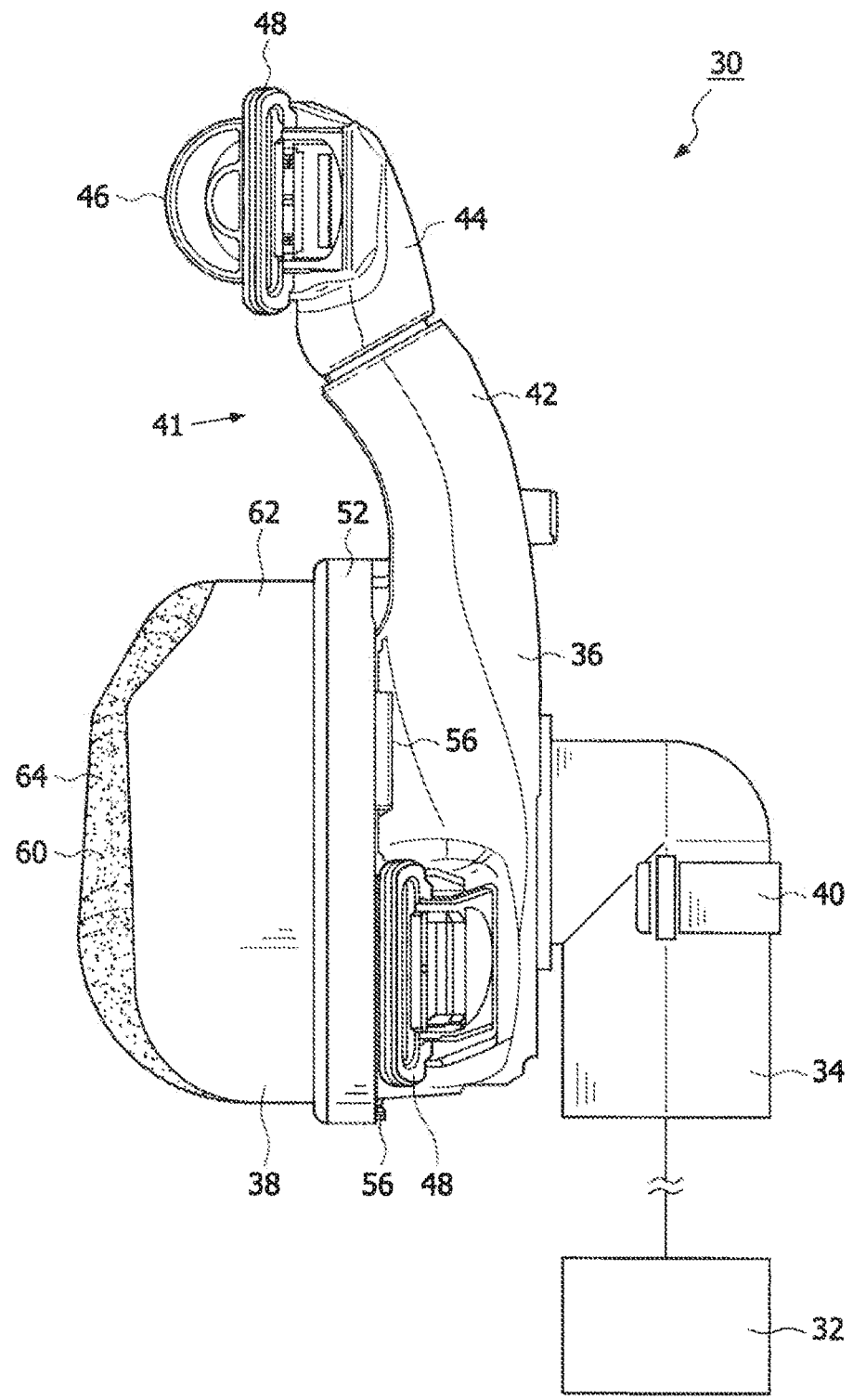
FIG. 2 is a side view of the mask shown in FIG. 1.
Figure 3:
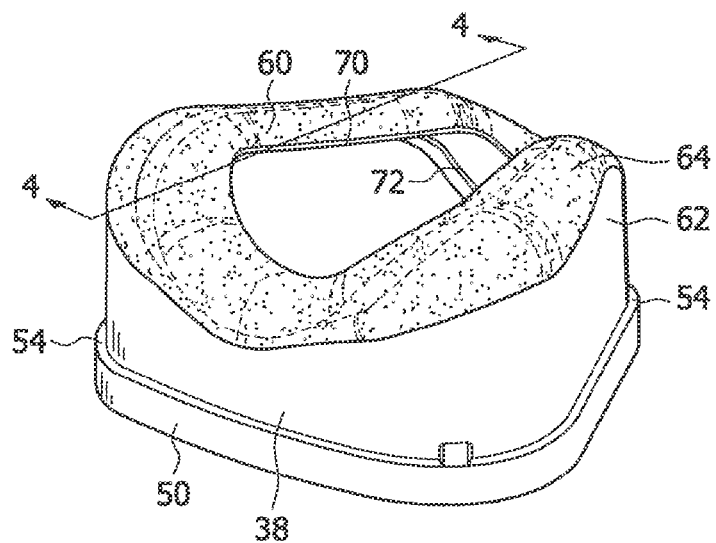
FIG. 3 is a perspective view of the seal used in the mask of FIG. 1.

FIGS. 1 and 2 illustrate an exemplary embodiment of a respiratory mask 30 according to the principles of the present invention. Mask 30 is shown schematically attached to a pressure generating system 32 via a patient circuit 34, as is conventionally known in the art. Respiratory mask 30 includes a shell 36 and a seal 38 attached to the shell. Patient circuit 34 is coupled to a port defined in a first side of the mask shell. Preferably, the patient circuit is connected to the mask shell so as to pivot or rotate relative to the mask shell and may or may not be detachable therefrom. In short, any conventional coupling technique for joining the conduit to the mask shell is contemplated by the present invention.

For purposes of the present invention, pressure generating system 32 is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

In the illustrated exemplary embodiment, an exhaust vent 40 is provided in patient circuit 34 for exhausting a flow of gas from the mask or conduit to ambient atmosphere. Such exhaust vents are conventionally used in pressure support systems that use a single-limb, i.e., a single conduit, to communicate a flow of gas to an airway of a patient. Thus, the present invention contemplates that exhaust vent 40 can be any conventional exhaust vent, and can be located on the mask, such as on the mask shell, on the patient circuit, at the mask shell/patient circuit interface, or at any combination of such locations. The exhaust vent shown in FIG. 2 corresponds to that described in published U.S. application Ser. No. 10/119,673, entitled, "Exhaust Port Assembly for a Pressure Support System," Publication No. US 2003/0005931, the contents of which are incorporated herein by reference.

Respiratory mask 30, including shell 36 and seal 38, can have any one of an infinite number of configurations, shapes, and sizes. In the illustrated embodiment, shell 36 corresponds to that described in U.S. application Ser. No. 10/654,379, entitled, "Patient Interface With Forehead Support System," the contents of which are incorporated herein by reference. Mask shell 30 is preferably formed from rigid plastic, such as polycarbonate. As described in detail in the '379 application, and as illustrated herein, mask 30 includes an adjustable forehead support 41. The forehead support is generally T-shaped and includes a support arm 42, which is slideably connected to a forehead support bracket 44. Forehead support bracket 44 includes a forehead pad 46 disposed on the patient contacting side to engage the forehead of the user. It is to be understood that the present invention contemplates that the forehead support assembly, and its individual components, can have any one of a variety of configurations. The present invention also contemplates that the forehead support assembly can be eliminated entirely.

In the illustrated embodiment, a headgear (not shown) attaches to mask 30 via headgear clips 48. Headgear clips 48 attach to headgear straps (not shown), for example by inserting the headgear straps into slots provided on the clips. The headgear clips are selectively attachable to the mask shell in any conventional manner. In this embodiment, the headgear clips attach to each side of forehead support bracket 44 and to each side of the lower portion of the mask shell. It can thus be appreciated that the headgear and head clip can have any configuration so as to be selectively attachable to the mask. It is to be further understood that the present invention contemplates eliminating all, or a portion, of the headgear clips an attaching the headgear straps to the mask shell.

Seal 38 includes a first end portion 50 that couples to mask shell 36. In the illustrated embodiment, first end portion 50 is generally triangular shaped and attaches to similarly-shaped opening provided in a second side of the mask shell. In this embodiment, the mask shell and the first end portion of the seal that attaches thereto are both generally planer, i.e., both line in a linear plane. It should be noted that the present invention contemplates that the mask shell and the first end portion of the seal can be contoured, when viewed in profile, so that first end portion 50, for example, does not lie in a common plane.

It is to be further understood that the present invention contemplates using any conventional technique for attaching the first end portion of the seal to the mask shell. Such techniques include permanently bonding the seal to the mask shell, for example, using adhesives, mechanical fasteners, or molding the seal onto the shell such that the seal is selectively detachable from the mask shell.

In the illustrated embodiment, a lock ring 52 slips over the seal and engages a lip 54 defined on the first end portion of the seal. The lock ring attaches to the mask shell in any conventional manner. For example, the present invention contemplates providing locking tabs 56 on lock ring 52 that selectively attach to engaging portions of the mask shell. When coupled to the mask shell, the seal defines a chamber for receiving a portion of the patient when the mask is donned by the patient. Typically, a portion of the patient, such as the patient's nose, inserts into the chamber so that the patient's airway is in fluid communication with the chamber.

Seal 38 includes a second end portion 60 for sealing engagement with a face of a patient. A sidewall 62 extends between first end portion 50 and second end portion 60. Seal 38 is preferably a unitary structure that attaches to a mounting portion of a mask shell or other support structure and provides a surface at second end portion 60 that contacts a surface of a patient. In the case of a nasal mask, for example, the second end portion contacts the area of the patient generally around the nose including over the bridge of the nose.

According to the principles of the present invention, a portion of the exposed surface of the seal at the second end portion includes a textured area 64, which is illustrated in the figures as a gray region at second end portion 60 of the seal. The remainder of the seal is non-textured, which is also referred to as being polished. Textured area 64 of seal 38 corresponds to an area in which the surface of the seal is intentionally roughened so as to have a greater amount of surface roughness than a surface that is considered to be polished, which is the case with the surface of the seal in conventional respiratory masks. In this embodiment, the surface roughness of textured area 64 is greater than the surface roughness at the other exposed surface of the seal, such as the exterior portion of sidewall 62.

The partial texturing of the seal eliminates or at least reduces the irritation caused by the polished surface of the cushion. This texturing provided at the patient contacting portion of the seal also helps prevent the seal from sticking to the skin. The texturing or increased surface roughness causes that portion of the seal to have a "silky" sensation, rather than a tacky or sticky feeling where there surface is more polished, i.e., has less surface roughness. Increasing the surface roughness provides this highly comfortable feel contact without having to change the seal in any other significant way.

For example, it is generally desirable to provide a clear silicone seal that is highly transparent due to the surface being polished, i.e., non-textured. Such as seal is generally transparent or opaque so that the seal has an overall "transparent look". This "transparent look" for the seal causes the seal to be perceived as being small and light-weight, which is more aesthetically pleasing that a heavy-looking seal. However, such a seal with its polished surfaces suffers from the disadvantages noted above. The present invention corrects these disadvantages while still retaining the desirable features associated with the use of a transparent looking, i.e., polished, seal. In other words, the present invention, by providing a portion of the seal that is textured and a portion that is not, obtains the benefits of the texturing, e.g., the silky feeling, as well as the benefits of non-texturing, e.g., the transparent, lightweight look for the seal.

Figure 4:
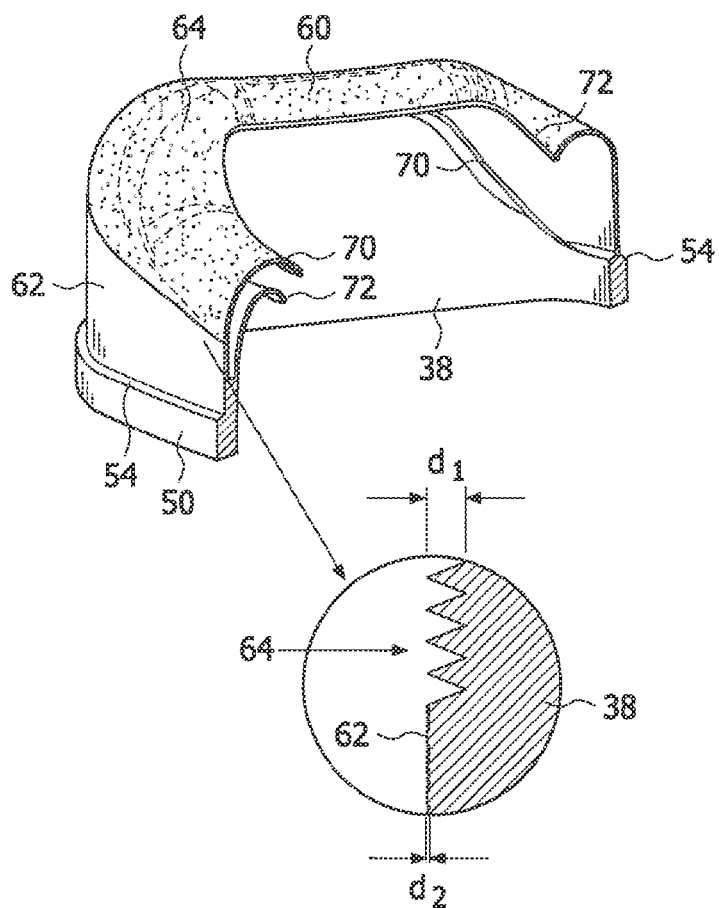
FIG. 4 is a sectional view of the seal taken along line 4-4 of FIG. 3 and also shows a detailed sectional view of one exemplary configuration for the surface roughness provided on the seal according to the principles of the present invention.

At a microscopic level, no surface appears perfectly smooth. All materials exhibit some degree of surface irregularities and bumps. One measurement of surface roughness is the rms (root-mean-square) of the height of the surface bumps, which is also referred to as the "rms roughness" or "rms surface roughness". This height is illustrated as distances $d_1$ and $d_2$ in FIG. 4. In an exemplary embodiment of the present invention, textured area 64 of seal 38 has an rms surface roughness greater than 700 microinches. That is, distance $d_1$ in FIG. 4 is generally greater than 700 microinches rms. In a more specific embodiment of the present invention, the textured area has an rms surface roughness in a range of 750-1,500 microinches. The polished surface, i.e., the non-textured surface, of the seal preferably has an rms surface roughness that is less than 690 microinches. That is, distance $d_2$ is generally less than 690 microinches rms, and is preferably in a range of 1-100 microinches rms.

A further embodiment of the present invention contemplates that the textured area 64 of seal 38 has an rms surface roughness greater than 10 micrometers (μm) which is equivalent to approximately 394 microinches (μin). In this embodiment, the polished surface, i.e., the non-textured surface, of the seal has an rms surface roughness that is 10 micrometers or less.

The present invention contemplates that increasing the surface roughness of a portion of the seal can be accomplished using any conventional technique. For example, one embodiment of the present invention contemplates using a high precision photo etching technique on the portion of the tool used to form this textured area of the seal. This photo etching increases the surface roughness of the tool where desired, so that the textured area is molded into the seal during the molding process. The non-textured area of the mold defines the polished surface of the seal. To those skilled in the art of molding, the polished mold is commonly referred to an SPI/SPE standard mold finish #1 (#3 Diamond Polish, RMS 0.5-1.0 microinches) and SPI/SPE standard mold finish #2 (#15 Diamond Polish, RMS 1.0-2.0 microinches).

The present invention also contemplates that the textured area can be formed on the seal after the seal molding process. That is, the seal can be formed such that all surfaces are polished, i.e., have an rms surface roughness less that 690, and the textured area is formed on the seal surface subsequent to the molding of the seal. Forming the textured area on the molded seal can be accomplished, for example, by cutting or scoring the seal with micro-abrasions. Forming the textured area on the molded seal can also be accomplished by adding a texturing on the seal, for example, by spraying or applying micro-particles on the molded seal. It is to be understood that the present invention is not intended to be limited to these exemplary techniques for forming the textured area on the molded seal. Quite the contrary, the present invention contemplates using any conventional technique for forming the textured area on the molded seal.

In the embodiment illustrated in FIGS. 1-4, the entire patient-contacting surface at the generally triangular-shaped second end portion of the seal includes the textured area of increased surface roughness. Textured area 64 is disposed around the entire perimeter of the patient contacting surface of the second end portion of the seal. This configuration ensures that the portion of the seal contacting the patient will include the texturing. It is be understood, that the present invention contemplates other configurations, patterns, and arrangements by which the textured area is disposed on the seal. For example, the present invention contemplates providing the textured area only at select locations on the seal, such as at the bridge of the nose or at the portion of the seal that underlies the nose. The discrete locations for the textured areas can be selected based on the desired performance characteristics for the seal and/or user preference. It can be appreciated that the myriad of possible configurations for the textured area are nearly infinite. Thus, no attempt is made to try to list the possible configurations other than to make note that there is no limit on such configurations.

It can also be appreciated that the shape of the seal and other features of the seal can be varied while still keeping within the spirit of the present invention. For example, in the embodiment illustrated in FIGS. 1-4, seal 38 is a two-flap seal. In this exemplary embodiment, a first flap 70 is operatively connected to side wall 62, and a second flap 72 is also operatively connected to the side wall underlying the first flap. It is to be understood that the first flap and the second flap need not be connected to the sidewall. Instead, they may individually and separately connect to the mask shell. In addition, the first flap and the second flap can have any desired configuration. The shapes and sizes of the first and second flaps can be complimentary to one another or entirely dissimilar. Although not shown, a third or more flaps can also be added if desired.

Figure 5:
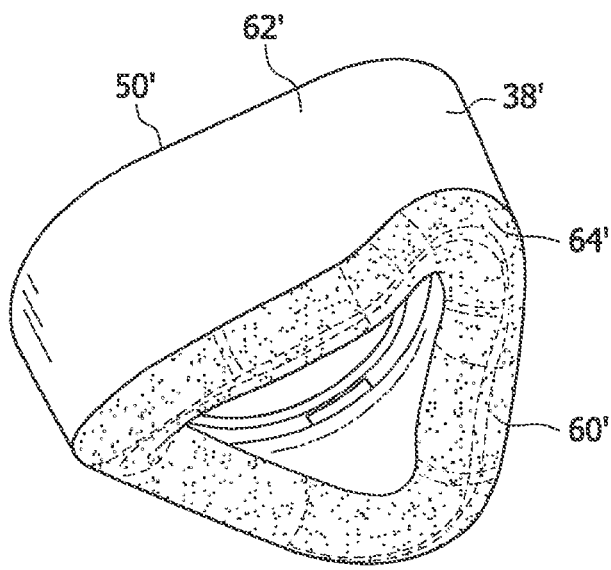
FIG. 5 is a perspective view of a second embodiment of a seal with a textured surface portion according to the principles of the present invention.

It is to be understood that the second flap may be entirely eliminated. A seal 38' showing a single flap configuration is shown, for example, in FIG. 5. Seal 38' is generally similar to seal 38 in FIGS. 1-4 except that it is a single-flap design. In addition, as seen in FIG. 5, seal 38' includes a first end portion 50' that is generally triangular shaped, a second end portion 60' for sealing engagement with a face of a user, a sidewall 62' that extends between first end portion 50' and second end portion 60', and a textured area 64'.

Figure 6A:
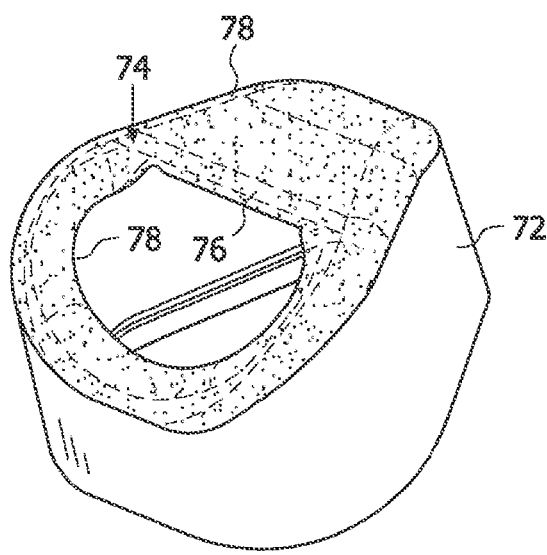
FIGS. 6A and 6B are perspective views of a third embodiment of a seal with a textured surface portion according to the principles of the present invention.
Figure 6B:
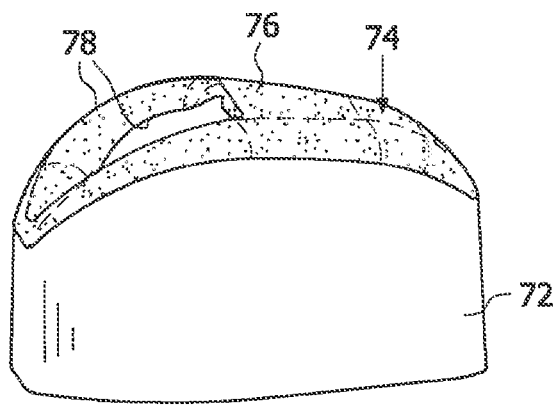

FIGS. 6A and 6B illustrate a third embodiment of a seal 72 with a textured surface 74 according to the principles of the present invention. A unique feature of seal 72 is that a flap 76 is provided at a second end portion 78 of the patient contacting area of the seal that overlies the bridge of the patient's nose. Flap 76 seals over the patient's nose when the mask having seal 72 is donned by the patient. The user's nose inserts into opening 78.

Figure 7A:
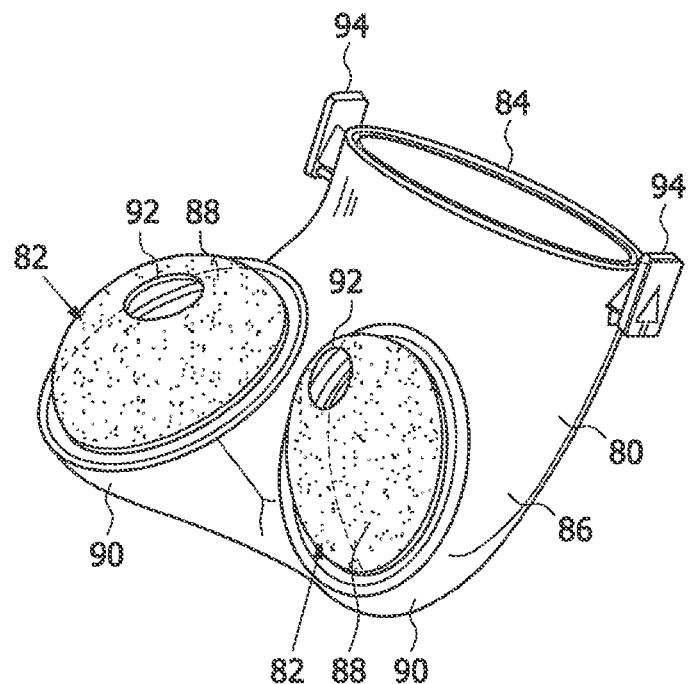
FIGS. 7A and 7B are perspective and side views, respectively, of a fourth embodiment of a seal with a textured surface portion according to the principles of the present invention.
Figure 7B:
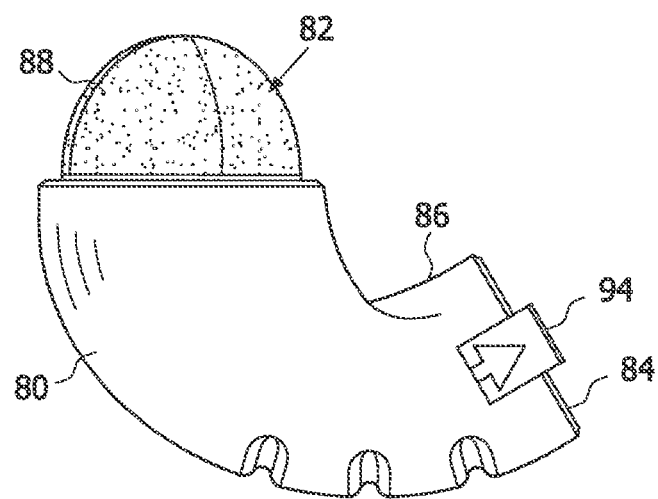

FIGS. 7A and 7B illustrate a fourth embodiment of a seal 80 with a textured surface 82 according to the principles of the present invention. This embodiment shows that the present invention contemplates providing the textured surface on other types of patient interface devices, not just on a traditional mask type device. Seal 80 is a nasal cannula type of patient interface device having a first end 84 that attaches to a seal support structure (not shown). Seal 80 correspond to the cannula-type nasal interface device shown and described in pending U.S. provisional patent application No. 60/496,059 filed Aug. 18, 2003 entitled, "Patient Interface Assembly and System Using Same", the contents of which are incorporated herein by reference.

Seal 80 includes a nasal cushion 86 and a pair of laterally spaced nares elements 88 at its distal end for insertion into the nostrils of the patient. The body of nasal cushion 86 includes a hollow chamber and extends from an oval shaped opening at first end 84 to laterally spaced outlet legs 90. Each outlet leg 90 is provided with one of nares element 88. The body of nasal cushion 86 curves about an axis substantially perpendicular to a plane separating the two nares elements. Each nares element 88 has an opening 92 to communicate with the nasal passages of the patient. Each of nares elements 88 is substantially dome-shaped having an elliptical base proportional to anthropometrical data of a nostril opening. Nasal cushion 86 is preferably formed from a soft cushiony material, such as silicone, appropriately soft thermoplastic elastomers, closed cell foam, or thin materials. Tabs 94 are provided on opposing sides of nasal cushion 86 to assist in aligning and securing the seal with a receiving end the seal support (not shown) of the cradle.

In the illustrated embodiment, textured area 82 is provided over substantially an entire area of dome-shaped nares elements 88. It is to be understood that the textured area can be provided over only a portion of each nares element in a select pattern or a select locations.

Figure 8:
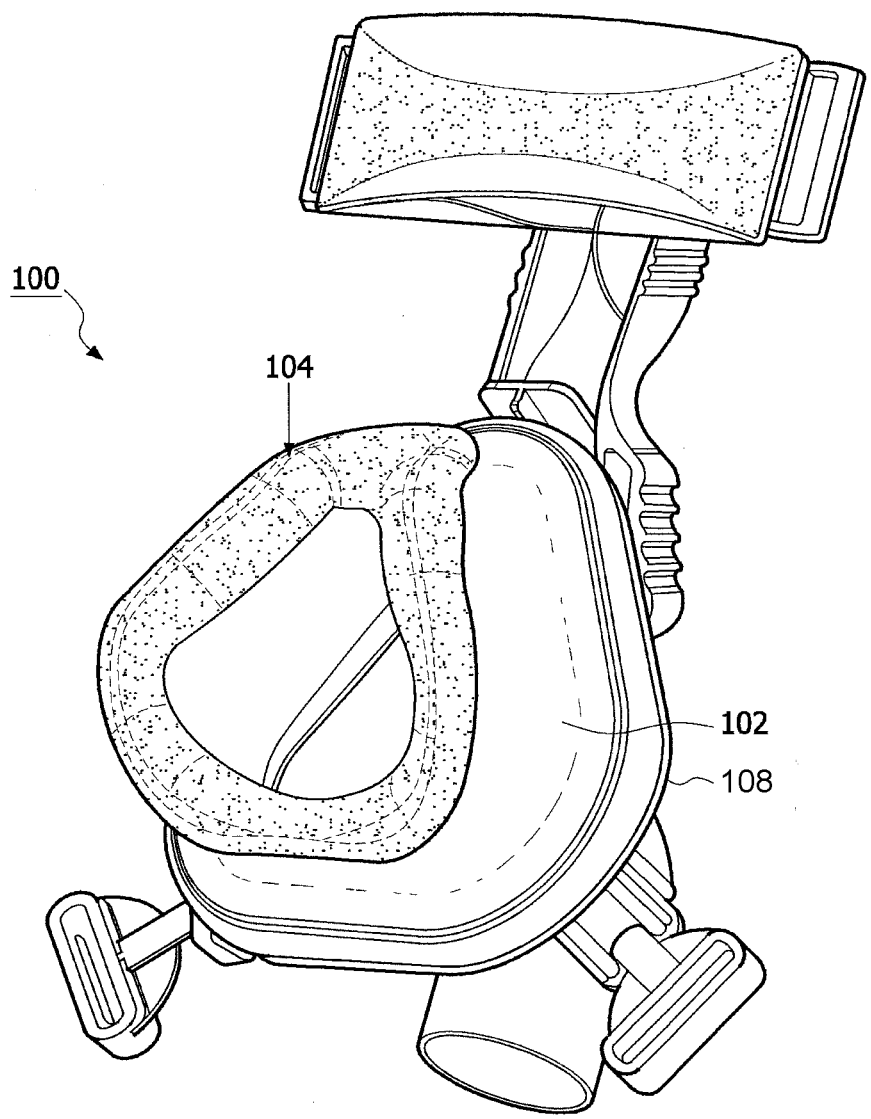
FIG. 8 is a perspective view of another respiratory mask having a seal with a textured surface portion according to the principles of the present invention.
Figure 9:
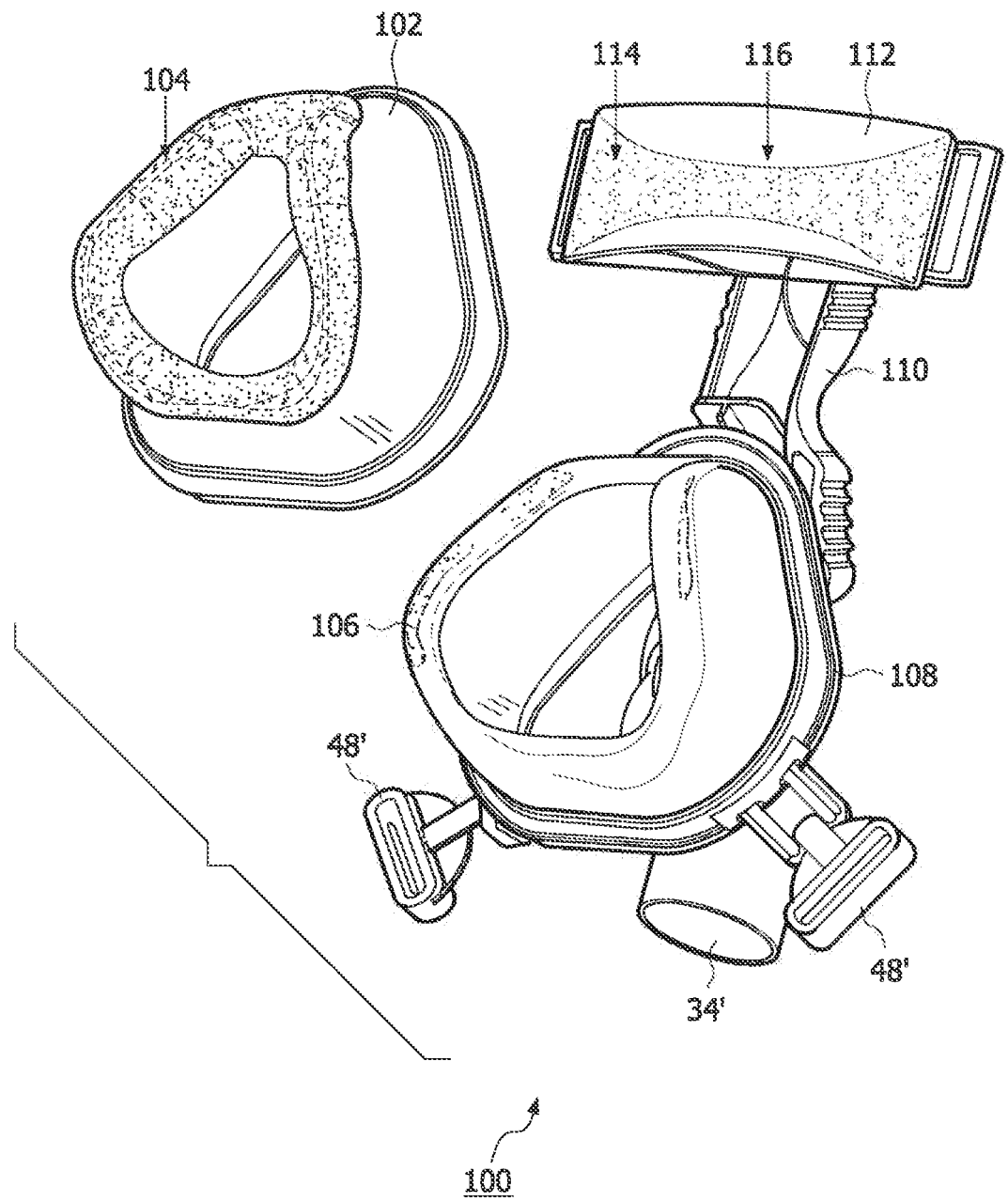
FIG. 9 is an exploded view of the mask shown in FIG. 8.

FIGS. 8 and 9 illustrate yet another respiratory mask 100 having a seal 102 with a textured surface area 104 according to the principles of the present invention. In this embodiment, seal 102 is disposed over a second seal 106, both of which are coupled to mask shell 108, either permanently or selectively. Second seal 106 can have any conventional configuration. However, a preferred exemplary embodiment contemplates that seal 106 is a gel seal of the type described in U.S. Pat. Nos. 5,647,357; 5,884,624; and 6,397,847 the contents of each of which are incorporated herein by reference.

Respiratory mask 100 can have any of a variety of configurations. However, in a preferred exemplary embodiment, respiratory mask 100 and its associated features correspond to the patient interface assemblies shown and described in pending U.S. patent application Ser. No. 10/654,379 entitled, "Patient Interface With Forehead Support System", filed Sep. 3, 2003, and Ser. No. 10/629,366 entitled, "Patient Interface and Headgear Connector" filed Jul. 29, 2003, the contents of both of which are incorporated herein by reference.

Respiratory mask 100 includes a forehead support 110 operatively coupled to mask shell 108. In a preferred embodiment, the forehead support is adjustable relative to the mask shell to control a position of the forehead support relative to the mask shell. A forehead pad 112 is disposed on the forehead support. At least a portion of the forehead pad includes a textured area 114 having an rms surface roughness as discussed above with respect to textured area 64. That is, in the illustrated embodiment, forehead pad 112 includes a textured area 114 and a non-textured area 116. It is to be understood that the surface of the forehead pad can be entirely textured, can have multiple textured areas, and the textured area or areas can have any one of a variety of different sizes, shapes, patterns, or configurations. In a preferred embodiment, the rms surface roughness of the textured area on the forehead pad is substantially the same as that of the textured area on the seal. It should also be noted that texturing can also be provided on the forehead pads shown in FIG. 1. In addition, as seen in FIG. 9, respiratory mask 100 includes a user circuit 34' and headgear clips 48'.

The present invention contemplates that the seal is a silicone rubber, or at least the portion of the seal that contacts the user is a silicone rubber. The texturing can be provided using one or more of a variety of technologies, such as laser texturing of injection molds, molding micro-spheres into the silicone, molding textile materials into the silicone, attachment a patch with the required texture to a surface of the seal. Still other techniques for forming the textured patterns are contemplated, such as laser etching the molded silicone, lithographic techniques, and any other technique that can be controlled so as to form a patterned or structured surface.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A respiratory mask comprising:
 (a) a shell;
 (b) a seal adapted to be coupled to the shell;
 (c) a forehead support operatively coupled to the shell; and
 (d) a patient contacting forehead pad operatively coupled to the shell, wherein at least a portion of the forehead pad includes an rms surface roughness greater than 10 micrometers.

2. The respiratory mask of claim 1, wherein the forehead pad includes a non-textured area having an rms surface roughness of 10 micrometers or less.

3. The respiratory mask of claim 1, wherein an entire user-contacting surface of the forehead pad has an rms surface roughness greater than 10 micrometers.

* * * * *